United States Patent [19]

Friedman et al.

[11] 4,057,567

[45] Nov. 8, 1977

[54] POLYMERIZATION METHOD AND T-ALKYL PERESTERS OF T-HYDROPEROXIDES FOR USE THEREIN

[75] Inventors: Ronald L. Friedman, San Rafael; Roger N. Lewis, Martinez, both of Calif.

[73] Assignee: Argus Chemical Corporation, Brooklyn, N.Y.

[21] Appl. No.: 333,904

[22] Filed: Feb. 20, 1973

Related U.S. Application Data

[63] Continuation-in-part of Ser. No. 157,683, June 28, 1971, Pat. No. 3,726,847, which is a continuation-in-part of Ser. No. 725,931, May 1, 1968, Pat. No. 3,624,123.

[51] Int. Cl.$^2$ ............................................. C07C 179/18
[52] U.S. Cl. ............................................. 260/453 RZ
[58] Field of Search .................................. 260/453 RZ

[56] References Cited

U.S. PATENT DOCUMENTS

| | | | |
|---|---|---|---|
| 2,661,363 | 12/1953 | Dickey | 260/453 R |
| 2,698,863 | 1/1955 | Dickey | 260/453 R |
| 3,264,274 | 8/1966 | Leveskis | 260/453 R |
| 3,326,859 | 6/1967 | Seiner | 260/453 R |
| 3,337,602 | 8/1967 | Guillet et al. | 260/453 R |
| 3,624,123 | 11/1971 | Lewis et al. | 260/453 R |

OTHER PUBLICATIONS

Friedman et al., "Chem. Structure vs. Activity of Peroxyesters," (1971), Mod. Plast. 48, pp. 66–68 (1971).

*Primary Examiner*—Glennon H. Hollrah
*Attorney, Agent, or Firm*—Townsend and Townsend

[57] ABSTRACT

Novel tertiary alkyl peresters of tertiary hydroperoxides are used as polymerization initiators wherein the peresters are characterized by the tertiary alkyl group of the acid moiety having at least two alkyl groups of two or more carbon atoms and the tertiary alkyl group of the hydroperoxide has at least five carbon atoms. Typical is the polymerization of certain vinyl monomers such as vinyl chloride.

5 Claims, No Drawings

POLYMERIZATION METHOD AND T-ALKYL PERESTERS OF T-HYDROPEROXIDES FOR USE THEREIN

This is a continuation-in-part of copending Patent Application Ser. No. 157,683, filed June 28, 1971, now U.S. Pat. No. 3,726,847, which in turn is a continuation-in-part of Patent Application Ser. No. 725,931, filed May 1, 1968, now U.S. Pat. No. 3,624,123.

This invention relates to polymerization using organic peroxide initiators. More particularly, it relates to certain t-alkyl peresters of t-hydroperoxides and their use in the polymerization of monomers such as vinyl chloride.

The above-referenced U.S. Pat. No. 3,624,123, incorporated herein by reference, discloses tertiary alkyl peroxyesters of neoacids in which the tertiary or alpha carbon atom relative to the carbonyl group of the acid has not more than one and preferably no methyl groups substituted thereon. With respect to the hydroperoxides which are reacted with these neoacids, the only tertiary alkyl hydroperoxide specifically disclosed is tertiary butyl hydroperoxide. It has now been discovered that analogous peresters formed from higher molecular weight tertiary alkyl hydroperoxides are surprisingly more efficient initiators for styrene, vinyl chloride, vinyl acetate and ethylene. The peroxyesters of this invention are organic peroxides of the formula:

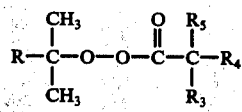

wherein $R_3$, $R_4$ and $R_5$ are the same or different alkyl groups of from 1 to 10 carbon atoms provided not more than one of $R_3$, $R_4$ and $R_5$ is methyl; and R is selected from 2,2-dimethyl propyl and straight chain alkyl of 2-5 carbon atoms.

The above-defined peroxyesters are prepared by the same procedures described in said U.S. Pat. No. 3,624,123 except that hydroperoxides of the formula:

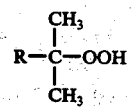

wherein R has the above definition are substituted for the hydroperoxides utilized in said patent. The present hydroperoxides may be reacted with any of the neoacids (conveniently in the form of the neoacid halide) defined in said patent and the peroxides of the present invention are obtained.

EXAMPLE I

This example illustrates the superior performance obtained by the use of peresters of 1,1,3,3-tetramethyl butyl hydroperoxide. The three peroxides shown in Table 1 were prepared in accordance with the procedures described in U.S. Pat. No. 3,624,123, particularly Examples I and II thereof. Peroxide #3, the neodecanoate perester, is an isomeric mixture formed by reacting 1,1,3,3-tetramethyl butyl hydroperoxide with the acid chloride of Enjay Chemical Company's neodecanoic acid which is stated by the manufacturer to have an isomer distribution of about 31% by weight alpha dimethyl substituted isomers, about 67% by weight of alpha-methyl, alpha-higher alkyl isomers and about 2% by weight of alpha dialkyl (higher than methyl) substituted isomers. The other peroxides in Table 1, numbers 1, 2 and 4 are single isomeric forms of the perester indicated and were obtained by reacting the hydroperoxide with the corresponding single acid chloride isomer. Peroxide numbers 1 and 2 represent the prior art as shown in U.S. Pat. No. 3,446,831 and are included for comparison. The peroxides obtained were then used in the production of polyvinyl chloride (PVC) in accordance with the following procedure.

Into a 6½ fluid ounce Coke bottle, containing 94.0 g of frozen dispersing solution, were added the appropriate amount of peroxide and 50.0 g of vinyl chloride monomer. The peroxides of Table 1 were added to the vinyl chloride monomer to comprise 0.03% by weight or 8.61 × 10$^{-5}$ moles thereof. The Coke bottle was capped, the contents almost melted, and then the bottle is placed in a rotating constant temperature bath for 6 hours at 50±0.5° C. After the bottle was cooled, and the excess monomer vented, the PVC was filtered, washed, and dried at 40°-50° C. for 12-16 hours. The results are as follows:

TABLE 1

| Peroxide | Avg. PVC Yield, g. | Avg. PVC Yield, % |
|---|---|---|
| 1. 1,1,3,3-tetramethylbutyl-perpivalate | 10.66 | 21.3 |
| 2. 1,1,3,3-tetramethylbutyl per 2,2-dimethyl valeroate | 27.16 | 54.3 |
| 3. 1,1,3,3-tetramethylbutyl per Neodecanoate | 32.12 | 64.2 |

EXAMPLE II

The initiators shown in Tables 2 and 3 were prepared by the procedures of U.S. Pat. No. 3,624,123 by reacting a hydroperoxide of the tertiary alkyl configuration shown in the peroxyester listed with an isomeric mixture of neodecanoyl chloride derived from the Enjay isomeric composition described in Example I hereof. The peroxyesters were then used to produce PVC in accordance with the following procedure.

6½ fluid ounce Coke bottles are used for polymerization at 50° C. The Coke bottles are prepared by weighing 94.0 g. of suspension solution into the bottles, freezing the suspension solution, adding the initiator as a 1 ml aliquot in odorless mineral spirits, and placing the stoppered bottles in the freezer overnight. The bottles are then filled with 50 g of inhibited vinyl chloride monomer (VCM). The monomer is purchased from Matheson Gas Products and contains 28-89 ppm phenol as inhibitor. After filling the bottles with VCM, they are capped and placed in a 40° C water bath until the ice is melted. They are then placed into a constant temperature bath at 50.0±0.5° C for the desired polymerization times. The bottles rotate at 25 RPM in the constant temperature bath. All initiator concentrations are adjusted to a 100% purity basis, and all bottles are run in duplicate at each concentration. The suspension solution is prepared by dissolving 16.92 Dow Methocel 65 HG (50 cps) and 15.00 g Na$_3$PO$_4$·12 H$_2$O in 14.10 liters of distilled water. The water to VCM ratio is 1.88 to 1 with 0.23 Dow Methocel 65 HG and 0.20 g Na$_3$PO$_4$·12 H$_2$O per 100 g VCM.

peroxide #1 of Tables 2 and 3 is the tertiary butyl peroxyester previously specifically disclosed in U.S. Pat. No. 3,624,123. The improved reaction rates and polymer yield of the peroxyesters of this invention are shown in Tables 2 and 3 by comparison therewith.

TABLE 2

| Initiator | % Wt. | (50.0±0.5° C, 6 Hrs.) Moles (× 10⁻⁴) | Wt. PVC, g. | Avg. Wt. PVC, g. | Avg. % Conversion |
|---|---|---|---|---|---|
| 1. t-butyl peroxyneodecanoate | 0.050 | 1.023 | 24.80 24.48 24.15 | 24.48 | 49.0 |
| 2. t-Amyl Peroxyneodecanoate | 0.051 | 1.023 | 31.50 31.11 31.57 | 31.39 | 62.8 |
| 3. t-Hexyl Peroxyneodecanoate | 0.053 | 1.023 | 32.15 32.11 | 32.13 | 64.3 |
| 4. t-Heptyl Peroxyneodecanoate | 0.055 | 1.023 | 30.51 31.38 30.92 | 30.94 | 61.9 |
| 5. t-Octyl Peroxyneodecanoate | 0.056 | 1.023 | 28.61 28.33 28.46 | 28.47 | 56.9 |

TABLE 3

| Initiator | % Wt. | Moles (× 10⁻⁵) | Reference | Time Hrs.2 | % Conversion 4 | 6 | 8 | 10 | 12 |
|---|---|---|---|---|---|---|---|---|---|
| 1. t-butyl peroxy-neodecanoate | 0.045 | 9.21 | 136–32 | 8.7 | 2.13 | 34.6 | 46.8 | 56.8 | 66.6 |
|  | 0.053 | 10.84 | 149.5 | 12.9 | 31.1 | 54.9 | 73.9 | 83.9 | 86.7 |
|  | 0.06 | 12.28 | 136–33, 38 | 16.0 | 36.7 | 65.1 | 84.4 | 86.1 | 87.9 |
| 2. t-Amyl Peroxy-neodecanoate | 0.02 | 3.87 | 1554–6 | 6.8 | 16.4 | 29.6 | 40.7 | 51.2 | 67.2 |
|  | 0.03 | 5.81 | 1554–6 | 9.9 | 27.1 | 42.8 | 59.5 | 76.6 | 87.6 |
|  | 0.04 | 7.74 | 1554–5 | 13.5 | 34.8 | 55.8[1] | 77.0 | 88.2 | 92.4 |
|  | 0.05 | 9.68 | 1554–5 | 17.3 | 43.2 | 66.3 | 87.4[2] | 92.9 | 93.2 |
| 3. t-Hexyl Peroxy-neodecanoate | 0.035 | 6.42 | 1575–42 | 11.6 | 29.5 | 45.9 | 64.0 | 79.8 | 86.1[2] |
|  | 0.045 | 8.26 | 1575–35 | 9.7[1] | 30.5 | 48.1 | 68.3 | 79.8 | 87.1 |
|  | 0.055 | 10.10 | 1575–32 | 17.1 | 43.6 | 65.7 | 84.9 | 88.7 | 90.3 |
| 4. t-Heptyl Peroxy-neodecanoate | 0.035 | 6.11 | 1575–42 | 8.5 | 25.9[2] | 42.5 | 58.4 | 73.1 | 81.3[2] |
|  | 0.045 | 7.86 | 1575–38 | 13.2 | 34.6[2] | 54.8 | 72.8 | 85.2 | 87.8 |
|  | 0.055 | 9.60 | 1575–32 | 13.8 | 39.2[2] | 60.0 | 79.6 | 86.8 | 88.9 |
| 5. t-Octyl Peroxy-neodecanoate | 0.045 | 7.49 | 1575–38 | 11.6[1] | 30.2 | 48.3 | 64.3 | 81.4 | 86.2 |
|  | 0.055 | 9.15 | 1575–35 | 11.8 | 32.4 | 51.1 | 69.2[1] | 80.8 | 85.9 |
|  | 0.065 | 10.82 | 1575–45 | 14.8 | 38.7 | 62.6 | 79.9 | 85.9 | 86.7 |

[1]Poor duplication.
[2]Single bottle value.

Aside from the selection of the perester having the structure discussed above, the practice of the present method in polymerization of styrene, vinyl chloride, vinyl acetate, and ethylene is consistent with prior art procedures for initiating the polymerization of such monomers. Thus, the present peresters are added in amounts generally comparable to those previously used and will usually fall within the range of about 0.005% to 3% by weight of the monomer content and more commonly about 0.01–0.5% by weight of the monomer content. For practical purposes the minimum amount of the perester is added which will effectively initiate the polymerization of the monomer mass. The usual conditions of temperature, pressure, solvents, and the like used in the polymerization of these monomers may be employed. In addition, it is contemplated that co-catalysts may be included to initiate the polymerization. For example, diacyl peroxides such as lauroyl peroxide may be used in combination with the present peresters as is understood in the art.

What is claimed is:
1. An organic peroxide of the formula:

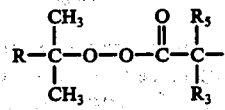

wherein $R_3$, $R_4$ and $R_5$ together with the associated tertiary carbon atom and adjacent carbonyl group form a neodecanoate group; and R is selected from 2,2-dimethyl propyl and straight chain alkyl of 2–5 carbon atoms.

2. An organic peroxide in accordance with claim 1 wherein R is ethyl.

3. An organic peroxide in accordance with claim 1 wherein R is n-propyl.

4. An organic peroxide in accordance with claim 1 wherein R is n-butyl.

5. An organic peroxide in accordance with claim 1 wherein R is n-amyl.

* * * * *